United States Patent
Santiago Fernandez et al.

(10) Patent No.: US 7,002,050 B2
(45) Date of Patent: Feb. 21, 2006

(54) PROCESS FOR PREPARING TERT-BUTANOL FROM ISOBUTENE-CONTAINING HYDROCARBON MIXTURES

(75) Inventors: Silvia Santiago Fernandez, Oberhausen (DE); Jörg Sauer, Dülmen (DE); Guido Stochniol, Haltern am See (DE); Dietrich Maschmeyer, Recklinghausen (DE); Wilfried Büschken, Haltern am See (DE); Klaus-Diether Wiese, Haltern am See (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 11/087,509

(22) Filed: Mar. 24, 2005

(65) Prior Publication Data

US 2005/0288534 A1    Dec. 29, 2005

(30) Foreign Application Priority Data

Jun. 26, 2004    (DE)    ................ 10 2004 030 943

(51) Int. Cl.
C07C 29/04    (2006.01)
C07C 29/03    (2006.01)

(52) U.S. Cl. .............. 568/896; 568/895; 568/897; 568/898; 568/899; 568/900; 568/901

(58) Field of Classification Search ............... 568/896, 568/895, 897, 898, 899, 900, 901
See application file for complete search history.

(56) References Cited

U.S. PATENT DOCUMENTS 6,111,148 A * 8/2000 Ogawa et al. ............. 568/399

* cited by examiner

*Primary Examiner*—Elvis O. Price
(74) *Attorney, Agent, or Firm*—Oblon, Spivak, McClelland, Maier & Neustadt, P.C.

(57) ABSTRACT

The present invention relates to a process for preparing tert-butanol (TBA) by reacting an isobutene-containing hydrocarbon mixture with water over a solid acid catalyst in a reactor cascade, wherein at least one reactor is supplied alternately with two different isobutene-containing hydrocarbon mixtures, of which one has both a higher tert-butanol content and a higher water content than the other mixture.

20 Claims, 2 Drawing Sheets

PROCESS FOR PREPARING TERT-BUTANOL FROM ISOBUTENE-CONTAINING HYDROCARBON MIXTURES

BACKGROUND OF THE INVENTION

1. Field of the Invention

The invention relates to a process for preparing tert-butanol by addition of water onto isobutene in the presence of an acid ion exchanger in a reactor cascade in which mixtures having different tert-butanol and water contents are fed alternately into at least one reactor.

2. Discussion of the Background tert-Butanol (TBA) is an important product which is prepared on a large industrial scale and is used as solvent and as intermediate for the preparation of methyl methacrylate. It is a precursor for the preparation of peroxides such as peroxy ketals, peresters or dialkyl peroxides having at least one tertiary butyl group. These compounds are used as oxidants and as initiators for free-radical reactions, for example olefin polymerization or crosslinking of plastics. tert-Butanol serves as intermediate for the recovery of pure isobutene from isobutene mixtures. Furthermore, it is a reagent for the introduction of tertiary butyl groups. Its alkali metal salts are strong bases which are used in many syntheses.

Tertiary butanol can be obtained by acid-catalyzed addition of water onto isobutene. Industrial isobutene mixtures frequently further comprise other olefins such as 2-butenes. If these starting materials are used, industrial processes employ conditions under which virtually only the isobutene and not the other olefins are hydrated and secondary reactions such as homo-oligomerization or heterooligomerization of the olefins are virtually completely suppressed. Such processes are usually carried out in the liquid phase and can be divided into two groups: a) processes in which the reaction is carried out in a water-containing catalyst solution and b) heterogeneous catalytic processes in which solid catalysts which are insoluble in the reaction phase are used.

The hydration of isobutene to tert-butanol with the aid of solid acid catalysts which are soluble neither in the starting materials nor in the products has the advantage that the reaction mixture is free of acid and can be worked up to obtain tert-butanol without losses caused by redissociation or by other secondary reactions. The reaction proceeds on the surface of the catalyst. For a reaction to take place, both reactants have to be present at the same time at the active site of the catalyst. This is made difficult by the fact that water and isobutene or an isobutene-containing hydrocarbon mixture are not miscible with one another. To obtain acceptable conversions, solvents which make a homogeneous mixture of water and isobutene starting mixture possible are used.

In DE 30 31 702 A1, methanol is described for this purpose as solvent both for water and for isobutene or an isobutene-containing hydrocarbon mixture. As products, tert-butanol and methyl tert-butyl ether are obtained side by side.

In EP 0 010 993 A1, aliphatic carboxylic acids having from 1 to 6 carbon atoms are used as solvents for both starting materials. In this case, the tertiary butyl esters of these acids are formed as by-products. These have to be hydrolyzed to tert-butanol and carboxylic acids.

Sulfolanes are used in DE 30 31 702 A1 and polyhydric alcohols of the neo type, for example neopentyl glycol, are used in U.S. Pat. No. 4,327,231. These solvents have to be separated off from the tert-butanol. In addition, there is a risk that the solvent used will decompose in a long-term operation.

To avoid these disadvantages, the target product, viz. TBA, is used as solubilizer in some processes. Such processes are described, for example, in WO 99/33775, DE 30 25 262 or DE 102 59 413.9. Here, a mixture of a hydrocarbon fraction in which isobutene is present, TBA and water is reacted over acid catalysts arranged in a fixed bed in a reactor cascade. The first reactor is usually operated in recirculation mode and the others are operated in a single pass. Water for the reaction can be added before each further reactor. The output from the last reactor is separated by distillation into a hydrocarbon mixture comprising the unreacted isobutene and crude TBA. Part of the crude TBA is recirculated to the first reactor. The other part can be utilized as such or worked up to give TBA and/or a TBA/water azeotrope.

In these processes, the TBA content increases when the isobutene content decreases from reactor to reactor due to progress of the reaction. The composition of the reaction mixture approaches the thermodynamic equilibrium between water, isobutene and TBA at a decreasing rate, so that complete conversion cannot be achieved. Conversions of about 93% can be achieved at long reaction times. However, if a higher space-time yield is desired, it is advantageous to limit the conversion. For example, it can be advantageous to limit the conversion when using industrial isobutene streams, for example raffinate I, to from 80 to 85%.

Patent application DE 103 38 581 describes the preparation of tert-butanol by reactingisobutene-containing hydrocarbon mixtures with water over solid acid catalysts in a plurality of reactors, with part of the TBA present in the reaction mixture being separated off upstream of the last reactor so as to increase the conversion. Despite this improvement, the total isobutene conversion at an approximately constant space-time yield increases by only 5–10% to about 90%.

Patent application DE 102 60 991 describes a process for preparing TBA in which a relatively complicated reactive distillation is used and in which high boilers are also formed from isobutene at virtually quantitative isobutene conversion.

SUMMARY OF THE INVENTION

The known processes which use solid, acidic substances which are insoluble in the reaction medium as a catalyst do offer a simple work-up but are not satisfactory in respect of space-time yield, yield and/or selectivity. Therefore, it is an object of the present invention to provide a process which gives a high space-time yield and/or a high selectivity at a high isobutene conversion.

It has surprisingly been found that a high space-time yield can be achieved together with good selectivity in the reaction of isobutene with water to form butanol in a reactor charged with solid acidic substances when the reactor is supplied alternately with a mixture of isobutene-containing hydrocarbon mixture; TBA and water; and an isobutene-containing hydrocarbon mixture having a lower water and TBA content.

The present invention accordingly provides a process for preparing tert-butanol (TBA) by reaction of an isobutene-containing hydrocarbon mixture with water over a solid acid catalyst in a reactor cascade (which has at least two reactors connected in series), wherein at least one reactor is supplied alternately with two different isobutene-containing hydrocarbon mixtures of which one has both a higher tert-butanol content and a higher water content than the other mixture.

The present invention also provides a tert-butanol-containing mixture obtainable by the process of the invention, in particular by a novel process as claimed in the claims.

The reactivity of an acid ion-exchange resin in the reaction of an olefin is dependent, inter alia, on the size of its hydration shell. Dry or virtually dry ion-exchange resin is highly reactive but has a low selectivity. It catalyzes not only the addition of water onto isobutene to form TBA but also the oligomerization of isobutene and other olefins present in the reaction mixture and the conversion of linear butenes into 2-butanol. In contrast, acid ion-exchange resin which is saturated with water has such a low reactivity that it does not catalyze the addition of water onto isobutene to any useful extent. The size of the hydration shell and thus the catalytic activity of the ion-exchange resin is dependent, inter alia, on the water content of the medium flowing round it. For this reason, the reaction of isobutene-containing hydrocarbon mixtures with water is carried out within particular concentration ranges. For example, DE 102 59 413.9 states that the conversion of a mixture comprising an isobutene-containing hydrocarbon mixture, TBA and water into TBA proceeds in a particularly advantageous fashion when the three-component mixture contains from 30 to 80% of the maximum amount of water made possible by the solubility of water in the mixture of TBA and the isobutene-containing hydrocarbon mixture.

It was therefore very surprising that a high conversion is achieved when one reactor is operated alternately using two different feed mixtures of which at least one has a composition outside the range indicated as optimal in the prior art. It was totally surprising that despite a hydrocarbon mixture which is low in water and TBA or virtually free of water and TBA being fed in, no decrease in the selectivity to the formation of TBA (considered overall over both operating states) was observed.

In the known industrial processes for preparing TBA, the concentration of isobutene decreases and the concentration of TBA increases in the reaction mixture from reactor to reactor due to the progress of the reaction. The composition of the reaction mixture approaches the thermodynamic equilibrium between isobutene, water and TBA at a rate which decreases from reactor to reactor.

To increase the conversion of isobutene into TBA in the process of the invention, the hydrocarbon fraction comprising the unreacted isobutene is separated off from the reaction mixture leaving the last reactor and all or some of this fraction is recirculated to at least one reactor, preferably the last reactor, with the proviso that this reactor is supplied alternately with the reaction mixture from the previous reactor and with, if appropriate, additional water or with the recirculated isobutene-containing hydrocarbon mixture as feed mixture. Since the recirculated isobutene-containing stream contains virtually no TBA, it is far away from the equilibrium between TBA, isobutene and water. Thus, a large part of the isobutene can be converted into TBA. Part of the hydration shell of the acid catalyst serves as water of reaction. Thus, the catalyst is partly dewatered by reaction of the isobutene-containing hydrocarbon fraction, resulting in its activity increasing. After switching over and supplying the reactor with a mixture of water and the output from the previous reactor, the reaction rate for the reaction of isobutene with water to form TBA is initially greater and then drops to the usual value as a consequence of water being taken up by the catalyst. Averaged over the two operating states, a higher space-time yield is obtained for this reactor than in the case of conventional operation.

The advantage of the present invention is that the conversion of isobutene and thus the yield of TBA is increased while the selectivity remains the same.

The process of the invention is described below by way of example without the invention, whose scope is defined by the claims and the description, being restricted by this. The claims themselves are also part of the disclosure of the present invention. If ranges or preferred ranges are indicated in the following text, all theoretically possible subranges within these ranges should also be considered to be part of the disclosure of the present invention, without these having been explicitly mentioned for reasons of simplicity.

The process of the invention for preparing TBA is based on the processes for preparing TBA described previously, e.g. in WO 99/33775, DE 30 25 262 or DE 102 59 413, with, in the process of the invention, at least one reactor being supplied alternately with two different isobutene-containing hydrocarbon mixtures having different water and TBA contents. The process parameters specified in the cited prior art for the preparation of TBA are therefore also part of the present description without explicit mention.

The process of the invention for preparing tert-butanol (TBA) by reaction of an isobutene-containing hydrocarbon mixture with water over a solid acid catalyst in a reactor cascade having at least two reactors is distinguished by at least one reactor being supplied alternately with two different isobutene-containing hydrocarbon mixtures of which one mixture (I) has both a higher tert-butanol content and a higher water content than the other mixture (II). The reactor which is supplied alternately with two different isobutene-containing hydrocarbon mixtures of which one has both a higher tert-butanol content and a higher water content than the other mixture is preferably the last reactor of the reactor cascade or a last reactor unit comprising two or more reactors connected in parallel of the reactor cascade.

Preference is given to feeding a hydrocarbon mixture having an isobutene content of greater than 25% by mass into the first reactor of the reactor cascade. As isobutene-containing feed mixture fed to the first reactor of the reactor cascade, it is possible to use an isobutene-containing hydrocarbon mixture or optionally pure isobutene in the process of the invention. The isobutene-containing hydrocarbon mixture preferably contains no acetylene derivatives and/or less than 5000 ppm of dienes and/or no further olefins having one or two branch(es) on the olefinic double bond. Particular preference is given to the isobutene-containing starting material having an isobutene content of from 25 to 100% by mass, more preferably from 30 to 99% by mass and very particularly preferably from 30 to 80% by mass.

Industrial mixtures comprising isobutene are, for example, light gasoline fractions from refineries, $C_4$ fractions from FCC units or steam crackers, mixtures from Fischer-Tropsch syntheses, mixtures from the dehydrogenation of butanes, mixtures from skeletal isomerization of linear butenes or mixtures formed by metathesis of olefins or from other industrial processes.

These mixtures can be used in the process of the invention, if appropriate after removal of multiply unsaturated compounds. For example, a suitable isobutene mixture can be obtained from the $C_4$ fraction from a steam cracker by extraction of the butadiene or by selective hydrogenation of the latter to linear butenes. This starting material (raffinate I or selectively hydrogenated cracker $C_4$) comprises n-butane, isobutane, the three linear butenes and isobutene and is a preferred starting material for the process of the invention. The isobutene content of the raffinate I which is preferably used is typically in the range from 30 to 60%.

Raffinate I, hydrogenated cracker $C_4$ or a hydrocarbon mixture having a similar composition can optionally be hydroisomerized in a reactive column. In this way, it is possible to obtain a mixture of isobutene (and possibly 1-butene) and isobutane which can then be used as raw material (stream (2)) in the TBA synthesis according to the invention.

The concentration of the isobutene in the hydrocarbon mixture can, as stated above, vary within a wide range. However, in the interests of the economics of the process, preference is given to using hydrocarbon mixtures having an isobutene concentration of greater than 30% by mass, more preferably greater than 40% by mass, as feed mixture.

As catalyst, preference is given to using an acid ion exchanger which is soluble neither in the feed mixture nor in the product mixture. The catalyst must not release acidic substances into the product mixture under the reaction conditions either as a result of hydrolysis or as a result of other reactions because this would lead to decreases in yield in the work-up of the reaction mixture.

The activity of suitable catalysts has to be such that under the reaction conditions they effect the hydration of isobutene but not to any significant extent that of unbranched olefins. Furthermore, the catalysts must not catalyze the oligomerization of olefins to any significant extent.

A group of suitable catalysts comprises solid ion-exchange resins bearing sulfonic acid groups. Particularly useful ion-exchange resins are, for example, resins produced by sulfonation of phenol/aldehyde condensates or of cooligomers of aromatic vinyl compounds. Examples of aromatic vinyl compounds for producing the cooligomers are: styrene, vinyltoluene, vinylnaphthalene, vinylethylbenzene, methylstyrene, vinylchlorobenzene, vinylxylene and divinylbenzene. In particular, the cooligomers formed by reaction of styrene with divinylbenzene are used as precursors for the preparation of ion-exchange resins having sulfonic acid groups. The resins can be produced in gel, macroporous or sponge form. Suitable resins of the styrene-divinylbenzene type are sold, inter alia, under the following trade names: Duolite® C-20, Duolite® C-26, Amberlyst® 15Wet, Amberlyst® 35Wet, Amberlite® IR-120, Amberlite® 200C, Dowex® 50, Lewatit® K2621, Lewatit® K2629 or Lewatit® VP OC 1505.

The properties of these resins, in particular specific surface area, porosity, stability, swelling or shrinkage and ion-exchange capacity, are variable and can be varied by means of the production process.

In the process of the invention, the ion-exchange resins are preferably used in their H form. The ion-exchange capacity is in the range from 2 to 7 eq/kg, in particular from 3 to 6 eq/kg (based on moist commercial resin). Preference is given to using macroporous resins, for example Amberlyst® 15Wet, Amberlyst® 35Wet, Lewatit® K2621, Lewatit® K2629 or Lewatit® VP OC 1505. The mean particle size of the resin is preferably from 0.5 to 2 mm. The particle size distribution can be narrow or broad. Preference is given to using ion-exchange resins having a very uniform particle size (monodisperse resins). When a plurality of reactors are used, these can be charged with resin of identical or different particle size (or particle size distribution).

The ion-exchange resins can optionally be used not only as spheres but also as shaped bodies, for example cylinders, rings or spheres, or polymerized onto shaped bodies.

It can be advantageous to use an ion-exchange resin having a relatively large particle size in reactors through which the reaction mixture flows at high linear velocities in order to reduce the differential pressure and use an ion-exchange resin having a smaller particle size in reactors through which the reaction mixture flows at a low linear velocity in order to achieve optimal conversion. In the reactors of the process of the invention, particularly preferably in those operated at a linear velocity of from 1 to 60 m/h, preference is given to using ion-exchange resins having a mean particle size of from 0.1 to 5 mm, preferably from 0.25 to 2 mm and very particularly preferably from 0.75 to 1 mm. At linear velocities of from 10 to 60 m/h, preference is given to using mean particle sizes of from 0.5 to 5 mm. At linear velocities of from 1 to 25 m/h, preference is given to using mean particle sizes of from 0.1 to 1 mm. An ion-exchange resin having a mean particle size in the range from 0.70 to 1 mm is, for example, Amberlyst® 35Wet from Rohm and Haas.

To prevent acidic groups being released from the resin during operation, which could cause problems in the work-up section of the process, and to maintain a high catalyst activity over a long period of time, the ion-exchange resin can be pretreated, for example by rinsing with water, TBA or TBA/water mixtures, preferably in a temperature range from 40 to 120° C.

It is possible to use the same catalysts or catalyst mixtures or different catalysts or catalyst mixtures in the reactors of the reactor cascade. Preference is given to all reactors of the reactor cascade being equipped with the same catalysts or catalyst mixtures.

The hydrocarbon mixture (II) having the lower tert-butanol and water content which is fed to the alternately operated reactor preferably contains less than or equal to 1% by mass of tert-butanol. The TBA content of this mixture is preferably less than or equal to 0.5% by mass, very particularly preferably less than or equal to 0.1% by mass. The water concentration of this mixture which is relatively low in water is not more than 10% greater, equal to or less than the maximum solution concentration (solubility) in the respective mixture. In the process of the invention, preference is given to using a homogeneous solution as mixture, i.e. the water concentration in the mixture (II) is equal to or less than the maximum possible solution concentration. It can be advantageous for the hydrocarbon mixture (II) having the lower tert-butanol content to have an isobutene content of from 1 to 30% by mass. As mixture (II) which is relatively low in water, preference is given to using a mixture which is obtained in the separation by distillation of the output from the alternately operated reactor(s) as overhead product in the separation of the TBA from the reactor output, with TBA or crude TBA being obtained as bottom product in the distillation.

The relatively water-rich mixture (I) which is fed alternately into the reactor comprises water, TBA and an isobutene-containing hydrocarbon mixture. The mixture (I) can be homogeneous or heterogeneous in the process of the invention. In the case of a heterogeneous mixture, part of the water is present in a second aqueous phase. Since the catalyst loses part of its hydration shell when the reactor is supplied with an isobutene-containing hydrocarbon stream which is low in water, more water has to be introduced into the reactor with the relatively water-rich feed mixture (I) than in the conventional mode of operation in order for sufficient water to be available to build up the hydration shell and as water of reaction. It can therefore be advantageous, depending on the ratio of hydrocarbon mixture to TBA and the other operating parameters, to feed in a heterogeneous mixture. The optimal water concentration in the starting material can be found by means of simple preliminary tests. The concentration of water in the mixture (I) is preferably at least 11%, more preferably at least 15% and particularly preferably at least 25%, greater than the maximum solution concentration (solubility) in the respective mixture. The concentration of water in the mixture (I) is very particularly preferably from 125 to 175% of the maximum solution concentration (solubility) in the respective mixture. As relatively water-rich mixture (I), it is possible to use, for example, the output from an upstream reactor in the reactor cascade, and it can likewise be advantageous to add additional water to this.

It is possible for one or more reactor(s) to be supplied alternately with two different isobutene-containing mixtures. If only one reactor is supplied alternately with two different mixtures (I) and (II), stock or buffer vessels can be provided in which the mixtures (I) and (II) are held at the ready in order to allow trouble-free continuous operation. For this reason, preference is given to at least two reactors or reactor units being operated alternately. If two or more reactors are supplied alternately with two different isobutene-containing mixtures, they can be connected in series or in parallel. Both or all of the two or more reactors can be supplied simultaneously with the mixture (II) which is relatively low in TBA or the mixture (II) which is relatively rich in TBA. To minimize the size of or to avoid stock or buffer vessels, it is particularly advantageous to provide at least two reactors connected in parallel so as to form a reactor unit in which the constituent reactors are supplied alternately with the two different isobutene-containing mixtures, with the mixture (I) being fed to one of the parallel reactors and the mixture (II) being fed at the same time to the other reactor at least at the beginning of each alternation cycle. If more than two reactors connected in parallel are present in a reactor unit, the connection and the switching from mixture (I) to mixture (II) or vice versa are dependent on the desired cycle time (period of time after which a reactor is switched over from one mixture to the other mixture (see explanations offered by way of example for the variants of the embodiments shown in FIG. 1)).

The two different outputs obtained from the alternately operated reactor(s) as a result of the alternate supply of different feeds to the reactor or reactors can together be separated in one distillation unit into, firstly, a hydrocarbon-containing stream which can comprise, in particular, unreacted olefins and saturated hydrocarbons and, secondly, crude tert.-butanol. At least part of the hydrocarbon-containing stream obtained in this separation is preferably reused as mixture (II) which is low in water and in TBA for supplying the alternately operated reactor(s). It is likewise possible for the two different outputs obtained from the alternately operated reactor as a result of the alternate supply of different feeds to the reactor to be fractionated separately in two distillation units to give hydrocarbon-containing streams and crude tert-butanol. In this case, at least part of the hydrocarbon-containing stream having the higher isobutene content obtained as overhead product is used for supplying the alternately operated reactor. The mixture (II) having a low TBA and water content obtained as overhead product, which is recirculated to the alternately operated reactor, preferably has an isobutene content of from 1 to 30% by mass, more preferably from 3 to 20% by mass, very particularly preferably from 5 to 12% by mass. The respective bottom fractions which comprise TBA, referred to as crude TBA, can be passed to a work-up, e.g. a distillation. Part of the bottom fraction can also be added to the starting mixture with which the first reactor of the reactor cascade is supplied.

If reference is made hereinafter to an alternately supplied reactor, this should also be taken as encompassing a plurality of reactors, in particular reactor units comprising two or more reactors connected in parallel.

The process is preferably carried out with the alternate supply to the reactor being effected so that the mixtures are changed in a cycle of from 0.5 to 10 hours. The cycle times for the two states of operation are preferably from 0.5 to 5 hours and particularly preferably from 1 to 2.5 hours. If cycle times of appreciably more than 10 hours are exceeded, the supply with low-water mixture (II) can lead to an excessively great increase in activity of the catalyst, which can lead to increased by-product formation. If the cycle time is significantly below 0.5 hour, the activity effect achieved by the formation or the degradation of the hydration shell around the catalyst is no longer observed.

The time ratio for the supply to the reactor (ratio of the cycle times to one another, i.e. the time for which the relatively water-rich mixture (I) is fed into the reactor to the time for which the mixture (II) which is low in water and TBA is fed in) can be equal to 1 or greater than or smaller than 1. A time ratio for the supply of mixture (I) which is relatively rich in water and TBA to the reactor to supply of mixture (II) which is relatively low in water and TBA of from 1.5:1 to 2.5:1 is preferably set. If ratios of the cycle times which are different from 1 are set in a reactor unit comprising at least two reactors connected in parallel in which the two different feed mixtures I and II are reacted in parallel, there are various possible ways of realizing this, of which three are described below by way of example:

a) The first reactor is supplied with mixture (I) for a time a. At the same time, the second reactor is supplied with the mixture (II) for a time b and subsequently with mixture (I) for a time c, with the sum of the times b and c corresponding to the time a. The ratio of the cycle times is thus (a+c)/b at a total cycle time of a.

b) If the respective starting materials (I) and (II) are interchanged, the time ratio of the supply is the reciprocal value.

c) In the case of a reactor unit comprising at least three reactors, it is possible, for example, for two reactors to be supplied with mixture (I) and one reactor to be supplied with mixture (II) in each case for a time a. The time ratio of the supply is thus 2:1. After the end of the cycle time, the supply is switched over so that the reactor which was supplied with mixture (II) in the last cycle is now supplied with mixture (I). One of the reactors which was supplied with mixture (I) in the last cycle, namely the reactor which was likewise supplied with mixture (I) in the last cycle but one, is now supplied with mixture (II), while the other reactor which was supplied with mixture (II) in the last cycle but one continues to be supplied with mixture (I) for one more cycle. At the next cycle change, the supply is correspondingly altered again.

The optimum conditions for the cycle times and cycle time ratio are dependent on the LHSV, the temperature and the composition of the two reactor feeds and can easily be determined by means of preliminary tests.

It has been found to be advantageous for the LHSV in the reactor which is operated alternately to be set to a value of from 0.1 to 5 h$^{-1}$, preferably from 0.4 to 3 h$^{-1}$ (liters of starting mixture per liter of catalyst per hour) when the relatively water- and TBA-rich mixture (I) is fed into the reactor. The LHSV for the isobutene-containing hydrocarbon mixture (II) which is low in TBA and water is preferably set to a value in the range from 0.1 to 4.5 h$^{-1}$ in particular in the range from 0.3 to 3 h$^{-1}$.

Since water is consumed by the hydration of isobutene, the water content of the reaction mixture decreases continually. To obtain a very high yield and reaction rate, it is advantageous to introduce further water. This can be achieved, for example, by feeding water in at various points on a tube reactor. However, it is in practice difficult to introduce precisely the required amount of water and to achieve immediate formation of a homogeneous solution. It is technically simpler and therefore advantageous to connect a plurality of reactors in series and to feed in the necessary amount of water before the reaction mixture enters each reactor, i.e., for example, between the reactors. In the case of the reactors of a reactor cascade which are not operated alternately, water is preferably fed in before the reaction mixture enters the respective reactor. The addition of water can be effected upstream of each reactor, with addition of water to the alternately operated reactor(s) not occurring at least when this/these is/are being supplied with the mixture which is low in water and TBA.

The water in the feed mixture preferably comes from a tert-butanol/water solution which is, except in the start-up phase, obtained in the process itself after removal of the hydrocarbons, e.g. by distillation, i.e. by recycling of part of the reactor output. If this amount of water is not sufficient, additional water (mains water, water of reaction or a mixture with tert-butanol) can be fed in. The amount of water in the mixture which is fed to a reactor is dependent on the ratio of TBA to the $C_4$-hydrocarbon mixture. With the exception of the alternately operated reactor, the amount of water introduced is preferably at most that amount which is soluble in the TBA/$C_4$-hydrocarbon mixture, so that a homogeneous solution is present. In particular, water contents of the TBA/$C_4$-hydrocarbon mixture which are lower than the respective maximum solubilities are set, except possibly for the last reactor. Very particular preference is given to setting water concentrations as claimed in the as yet unpublished patent specification DE 102 59 413.9 or DE 103 30 710.9. As stated above, pure water or a mixture with tert-butanol can be introduced into the reactors. It is also possible for part of the TBA obtained by means of the reaction to be recycled for producing a homogeneous mixture with water and the isobutene-containing hydrocarbon mixture.

The temperatures at which the process of the invention is carried out are preferably from 30 to 120° C. At lower temperatures, the reaction rate is too low and at higher temperatures secondary reactions, for example the oligomerization of the olefins, occur to an increased extent. The reactors are preferably operated in the temperature range from 35 to 80° C. The temperatures in the various reactors can be identical or different within the indicated range. In a preferred process variant, successive reactors are each operated at a lower temperature than the preceding reactor. Since the position of equilibrium becomes more advantageous as the temperature drops, a higher conversion can be achieved in this way. However, it is not practical to reduce the temperature below 35° C., since the reaction then becomes too slow for an industrial process. The alternately operated reactor or the alternately operated reactor unit can, depending on the feed mixture, be operated at identical or different temperatures after each change.

Each reactor can be operated adiabatically or pseudoisothermally, i.e. with a temperature difference from reactor inlet to reactor outlet of less than 10 K, preferably less than 5 K and particularly preferably less than 1 K. An excessively high temperature increase is to be avoided because of the unfavorable effect on the equilibrium (redissociation) and the increase in secondary reactions. Preference is given to all reactors of the reactor cascade being operated with a temperature difference of the reaction mixture from reactor inlet to reactor outlet of less than 10 K. The temperature can be set or kept essentially constant by introduction or removal of heat by means of suitable apparatuses, e.g. reactors having walls configured as heat exchangers.

The reaction according to the invention can be carried out at a pressure equal to or above the vapor pressure of the hydrocarbon feed mixture at the respective reaction temperature, preferably at a pressure below 40 bar. To avoid vaporization problems in the reactors, the pressure should be from 2 to 4 bar higher than the vapor pressure of the reaction mixture.

The process can be carried out in batch reactors or continuously operating reactors as are customarily used for solid/liquid contact reactions. When continuously operating flow reactors are employed, use is preferably but not necessarily made of a fixed bed. If a fixed-bed flow reactor is used, the liquid can flow upward or downward. Downward flow of the liquid is usually preferred. Flow through the alternately operated reactor or the alternately operated reactor unit is preferably likewise from the top downward.

Furthermore, it is possible for the reactor to be operated with partial recirculation of product (recirculation mode) or in a single pass. If one or more of the reactors are operated with recirculation of product, a recycle factor (ratio of quantity pumped around the circuit to fresh feed) of from 0.1 to 10 is preferably set. The recycle factor for the first reactor is preferably from 1 to 5, in particular from 2 to 3.5. In a preferred embodiment of the process of the invention, the first reactor can be operated with recirculation of product and the further reactors or reactor units can be operated in a single pass, with the last reactor (reactor unit) in particular being operated alternately. The number of reactors used is preferably from 2 to 10, very particularly preferably from 3 to 5 (for this purpose, a reactor unit counts as one reactor).

When tube reactors are used, the ratio of length to diameter of the catalyst bed can be varied, either via the geometric dimensions of the reactor or via its degree of fill. Different superficial velocities can thus be achieved at a constant amount of catalyst and throughput (LHSV). Reactors in which part of the reaction mixture is recirculated can be operated, for example, at superficial velocities of from 12 to 60 m/h, preferably from 12 to 30 m/h. In reactors operated in a single pass, the superficial velocities can be in the range from 0.8 to 55 m/h and particularly preferably in the range from 1 to 25 m/h.

The space velocity of the catalyst (LHSV) in reactors which are operated with recirculation of product is preferably from 0.3 to 10 h$^{-1}$, more preferably from 1 to 6 h$^{-1}$ and particularly preferably from 2 to 5 h$^{-1}$. In the case of reactors which are operated in a single pass, the space velocities are preferably in the range from 0.1 to 5.0 h$^{-1}$, more preferably in the range from 0.4 to 3 h$^{-1}$ and particularly preferably in the range from 0.6 to 2 h$^{-1}$.

The process of the invention is carried out in a reactor cascade having at least one alternately operated reactor or at least one alternately operated reactor unit which can in each case have identical or different reactor temperatures. In this context, a reactor unit comprises one or two reactor(s) connected in parallel which can be supplied alternately with two different mixtures. The process is preferably carried out in a plurality of reactors or reactor units connected in series which have temperatures which decrease in the flow direction.

The process of the invention can be carried out in various embodiments. Two preferred embodiments of the present invention are shown by way of example as block diagrams in FIG. 1 and FIG. 2. These schematic diagrams each have three reactors or reactor units. It goes without saying that the process of the invention for preparing TBA can also be carried out using two or more than three reactors (or reactor units).

Figure 1:
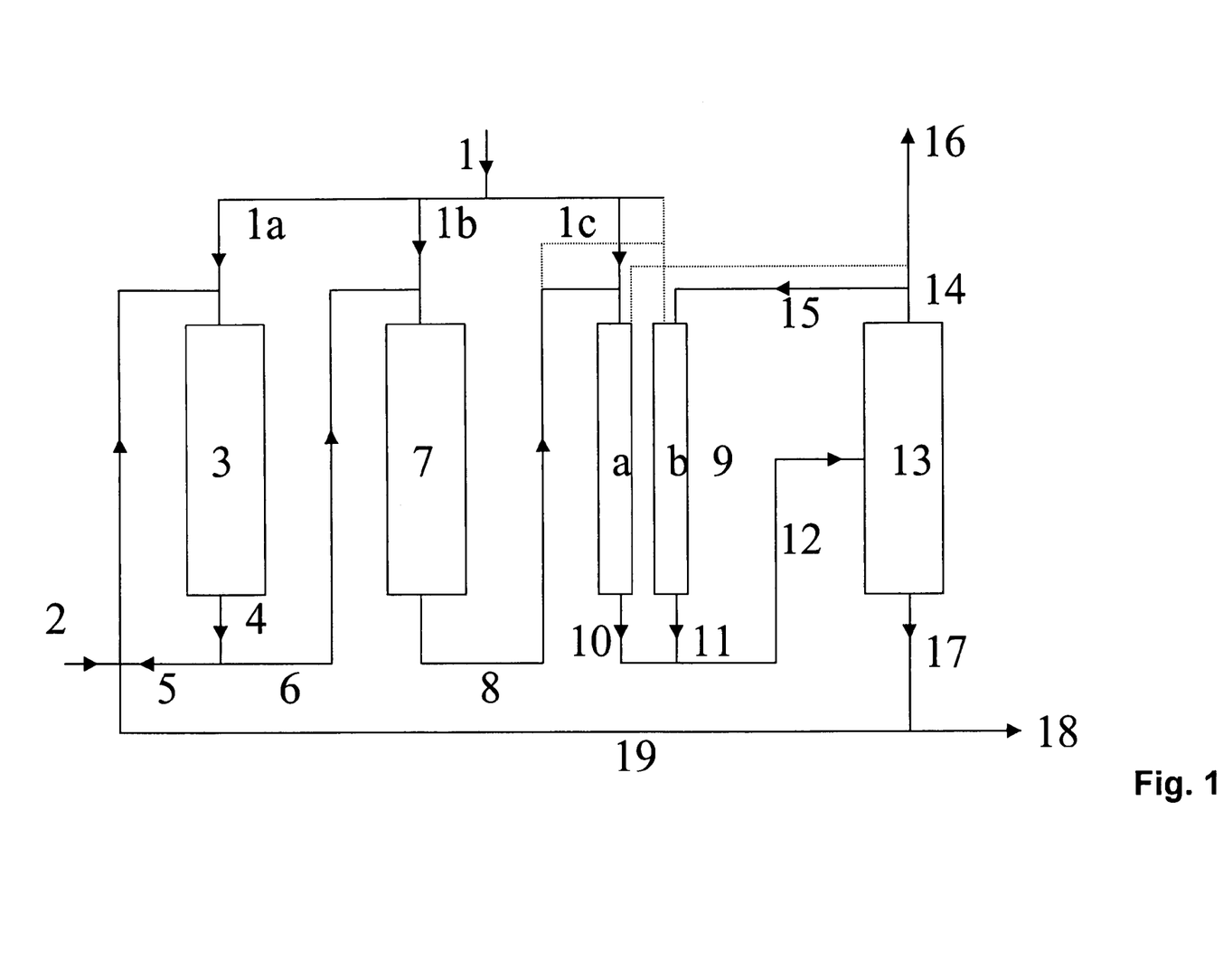
FIG. 1 shows a schematic diagram of one embodiment for carrying out the process described herein.

In the first embodiment of the process of the invention as shown in FIG. 1, water of reaction (1a), isobutene-containing hydrocarbon feed mixture (2), crude TBA (19) and part (5) of the output (4) from the reactor (3) are fed into the reactor (3). Part (6) of the output (4) is reacted together with water of reaction (1b) in the second reactor (7). The output (8) from the reactor (7) is fed together with water of reaction (1c) either into the reactor (9a) or, after switching over, into the reactor (9b). Part (15) of the overhead product (14) from column (13) is fed either into the reactor (9b) or, after switching over, into the reactor (9a). If appropriate, part of the water in stream (15) is removed in an apparatus which is not shown. For example, water present in heterogeneous form can be separated off with the aid of a decanter. The two outputs (10) and (11) from the two reactors (9a) and (9b) are combined and fed as stream (12) into the distillation column (13) and separated there into, firstly, an overhead product (14) comprising isobutene and other low-boiling hydrocarbons and, secondly, crude TBA (17). Part (16) of the overhead product (14) is separated off to bleed off hydrocarbons. Part (19) of the crude TBA (17) is recirculated to the reactor (3). The other part (18) can be worked up in a plant which is not shown to give pure TBA and/or TBA/water azeotrope. The work-up can be carried out, for example, by distillation or extraction. To level out the composition of the stream (12), it can be advantageous to provide a buffer vessel (not shown) for this stream, so that the mixed outputs from the reactors can be conveyed from this buffer vessel into the distillation column (13).

In the embodiment of the process of the invention shown in FIG. 1, the two reactors (9a) and (9b) can in one variant be replaced by a single reactor (9). This is supplied alternately either with a mixture of stream (8) and water of reaction or with the distillate (15). In this variant shown in FIG. 1, additional buffer vessels (not shown in FIG. 1) for the streams (8), (10), (11) and (15) can make trouble-free continuous operation possible. To be able to set a cycle ratio different from 1, it is likewise preferred to operate according to this variant or a further variant of the plant shown in FIG. 1 in which a third reactor 9c is present can be provided. A cycle ratio of 2:1 can be set by appropriate further switching so that water and mixture from stream 8 are firstly fed into the reactors 9a and 9b and at the same time distillate 15 is fed into reactor 9c. After the cycle time has elapsed, the distillate is then fed to the reactor 9b while the reactors 9a and 9c are supplied with water and the mixture from stream 8 during this cycle. After the cycle time has elapsed, the system is again switched over so that the distillate is then fed to the reactor 9a while the other reactors are supplied with water and stream 8. After the end of this cycle, the system is switched back to the first cycle. To set further cycle ratios different from 1, it is possible, regardless of whether two or more reactors are present, to switch over at least one reactor to the other starting material even before the end of the actual cycle. In this way, any ratios can be set. The possible ways just described of varying the cycle ratio in the case of two or more reactors are not limited to plants as shown in FIG. 1 or their variants, but can be employed generally in the process of the invention.

Figure 2:
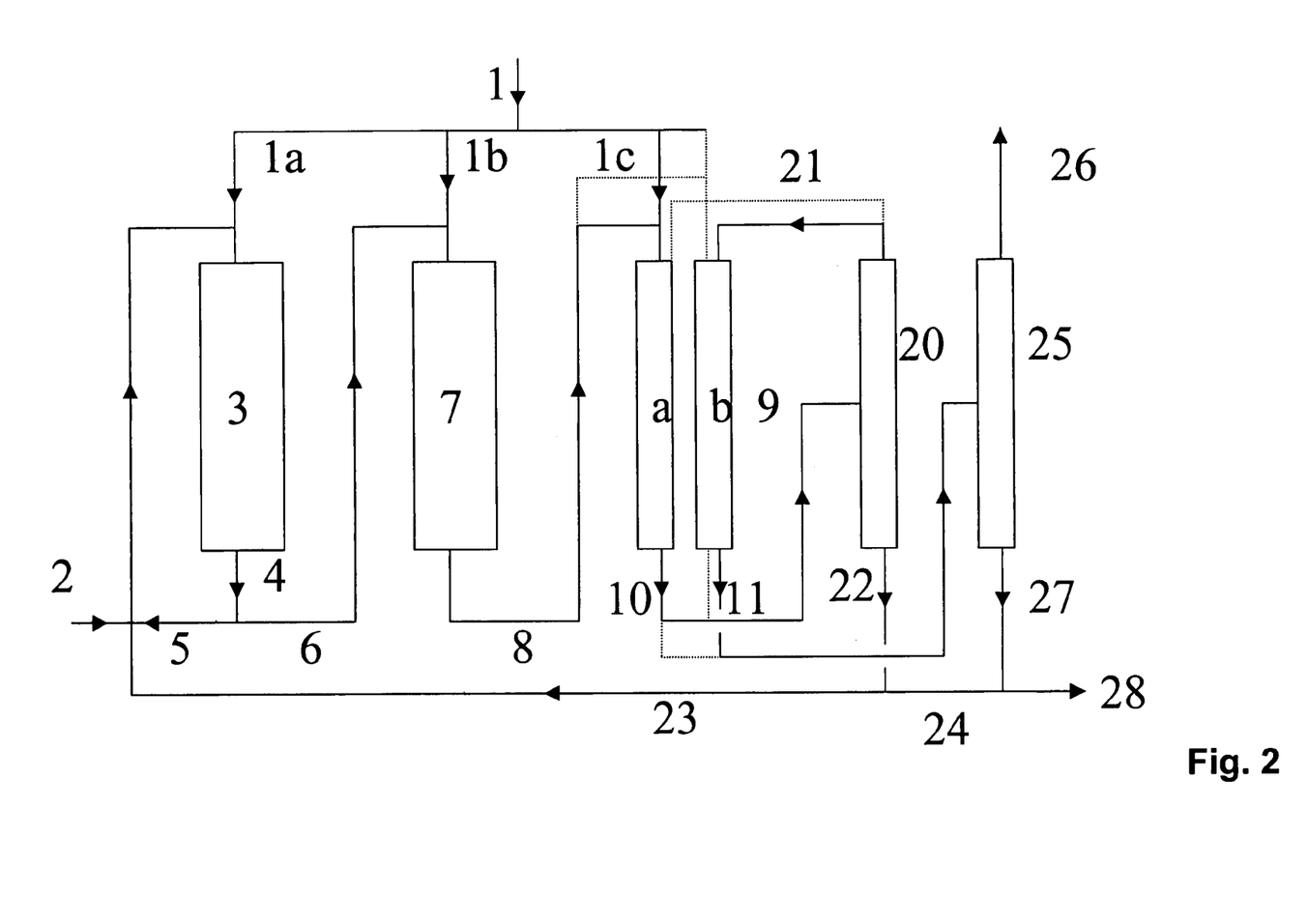
FIG. 2 shows another schematic diagram of one embodiment for carrying out the process described herein.

In the second embodiment of the process of the invention as shown in FIG. 2, water of reaction (1a), isobutene-containing hydrocarbon feed mixture (2), crude TBA (23) and part (5) of the output (4) from the reactor (3) are fed into the reactor (3). Part (6) of the output (4) is reacted together with water of reaction (1b) in the second reactor (7). The output (8) from the reactor (7) is fed together with water of reaction (1c) either into the reactor (9a) or, after switching over, into the reactor (9b). The overhead product (21) from column (20) is fed either into the reactor (9b) or, after switching over, into the reactor (9a). The reactor output (10) or (11) is, if it has been formed by reaction of stream (8) with water of reaction (1c), fed to the column (20). The reaction output (10) or (11) is, if it has been formed by reaction of the distillate (21) from the column (20), fed to the column (25). In the column (20), the output (10) or (11) is separated into, firstly, an isobutene-containing hydrocarbon mixture which is, if appropriate after removal of water in an apparatus which is not shown, for example a decanter for separating off water present in heterogeneous form, recirculated to the reactor (9a) or (9b) and, secondly, crude TBA (22). In column (25), the output (10) or (11) is separated into, firstly, an overhead product (26) which contains less isobutene than the distillate (21) and, secondly, and crude TBA (27). Part (23) of the crude TBA produced (stream (22) or stream (27) or a mixture of stream (22) and stream (27)) is recirculated to the reactor (3). The other part (28) can be worked up in a plant which is not shown to give pure TBA and/or TBA/water azeotrope. The stream (26) is discharged and can be worked up in other plants by known methods, e.g. by distillation.

In embodiment 2, in which the two different outputs from the alternately operated reactor or the alternately operated reactor unit are worked up in two different distillation units, it is advantageous to carry out the switching over of the reactor outputs to the two distillation units with a certain time delay after switching over the reactor feeds. The optimum magnitude of the time difference between the switching over of the feeds and the outputs is dependent, inter alia, on the reactor throughput (LHSV) and can easily be determined by monitoring the composition of the reactor outputs. The outputs are therefore preferably switched over automatically or semiautomatically at times which are functions of the switching over of the feeds or according to on-line measurement of the composition of the output or on-line measurement of the concentration of one component, in particular the concentration of water or TBA.

A delayed switching over of the feeds and outputs as just described is not restricted to the embodiment described in FIG. 2 but can be provided quite generally whenever the reactor outputs from the alternately operated reactors are conveyed to two different distillation columns for fractionation.

In a process of the type shown in FIG. 2, it is advantageous to provide buffer vessels for the feeds to the columns (20) and (25) in order to aid continuous operation.

It may be pointed out that in this second embodiment, too, the reactors (9a) and (9b) can in one variant be replaced by a single reactor or be supplemented by one or more further reactor(s) in a manner analogous to the embodiment shown in FIG. 1.

The embodiment of the process shown in FIG. 2 differs from the embodiment shown in FIG. 1 essentially in that the embodiment of FIG. 2 has one more distillation stage and the two different product outputs of the alternately operated reactor/reactors are fractionated in two different columns. As a result, a higher isobutene conversion can be achieved by means of a process operated according to the embodiment of FIG. 2 than in a process as shown in FIG. 1. However, a process operated according to the embodiment shown in FIG. 2 has a higher capital requirement and higher operating costs.

When a still higher isobutene conversion to TBA than in a process operated according to the embodiment shown in FIG. 2 is desired, the isobutene-containing distillate (26 in FIG. 2) can optionally be used for alternate supply to a further reactor (for example reactor 7 in FIG. 2) and the resulting product can be separated in a third column (not shown in FIG. 2).

The present invention is described by way of example in the following examples without the invention being restricted to the embodiments presented in the examples.

EXAMPLES

The experiments were carried out in a tube reactor having an internal diameter of 2.1 cm and a length of 40 cm. This contained 120 ml of Amberlyst® 35 Wet ion-exchange resin in the H form in all experiments. In all experiments, the reaction mixture flowed through the reactor from the top downward. The reactor was in each case operated isothermally at 55° C. and a reaction pressure of 15 bar, so that the feed and product mixtures were virtually exclusively liquid.

The experiments were carried out using a raffinate stream (X) which was low in isobutene and had the following composition:
n-butane 15.4% by mass
isobutane 1.4% by mass
1-butene 31.3% by mass
2-butene (cis and trans) 46.6% by mass
isobutene 5.3% by mass In the interests of simplicity, the $C_4$-hydrocarbons other than isobutene are referred to as miscellaneous $C_4$ in the following text. The feed mixture (Xb) was prepared from the mixture (X=Xa) by mixing in TBA and water. Mixing of mixture (Xa) with mixture (Xb) in a ratio of 47:61.6 gave the feed mixture (Xc).

TABLE 1

Composition of the feed mixtures.

| Designation | Composition in % by mass |
|---|---|
| Xa (homogeneous) | 5.32 isobutene<br>94.68 miscellaneous $C_4$ |
| Xb | 4.06 isobutene<br>72.27 miscellaneous $C_4$<br>17.74 TBA<br>5.60 water<br>0.334 other materials |
| Xc | 4.60 isobutene<br>81.95 miscellaneous $C_4$<br>10.06 TBA<br>3.18 water<br>0.21 other materials |

The analysis of the composition of the feed and/or product mixtures was carried out by gas chromatography on a DB1 column (Agilent J&W). Since the various $C_4$ components cannot be separated on the DB1 column, the make-up of the $C_4$ component was analyzed on an $Al_2O_3/Na_2SO_4$ column from Chrompack.

Example 1

According to the Invention

The reactor was supplied alternately with the mixtures (Xa) and (Xb). The cycle time was 4 hours. Thus, the mixture (Xa) was fed in for the first four hours, the mixture (Xb) was fed in for the next four hours, the mixture (Xa) was fed in again for the following four hours and so forth. The feed rate for the mixture (Xa) was 47 g/h and that for the mixture (Xb) was 61.6 g/h. The mixture was collected for 48 hours (6 cycles of mixture (Xa) and 6 cycles of mixture (Xb)) and an average analysis of this mixture was then obtained.

The heterogeneous sample had the following composition (in % by mass):
4.19 isobutene
81.95 miscellaneous $C_4$
10.62 TBA
3.04 water
0.2 other materials The isobutene conversion calculated therefrom was 9.2%.

Example 2

Comparative Example

The feed mixture (Xc) was fed into the reactor. The feed rate was 54.3 g/h. The output from the reaction was collected for 48 hours and an average analysis was obtained.

The output from the reaction had the following composition (in % by mass):
4.40 isobutene
81.95 miscellaneous $C_4$
10.33 TBA
3.11 water
0.21 other materials The isobutene conversion calculated therefrom was 4.6%.

In both of the experiments, the same molar amount of each component was fed into the reactor over a period of 48 hours. However, the experiment in Example 1 according to the invention gave an isobutene conversion which was twice that in the experiment in the comparative example (Example 2).

The present application claims priority to German patent application DE 102004030943.4 filed Jun. 26, 2004, the entire contents of which are incorporated herein by reference.

What is claimed is:

1. A process for preparing tert-butanol, comprising reacting an isobutene-containing hydrocarbon mixture with water over a solid acid catalyst in at least one reactor, wherein the at least one reactor is supplied alternately with at least two different isobutene-containing hydrocarbon mixtures, and wherein at least one first isobutene-containing hydrocarbon mixture has a higher tert-butanol content and a higher water content than a at least one second isobutene-containing hydrocarbon mixture.

2. The process as claimed in claim 1, wherein the at least one second isobutene-containing hydrocarbon mixture has less than 1% by mass of tert-butanol.

3. The process as claimed in claim 2, wherein the at least one second isobutene-containing hydrocarbon mixture contains less than 0.1% by mass of tert-butanol.

4. The process as claimed in claim 1, wherein the at least one second isobutene-containing hydrocarbon mixture has an isobutene content of from 1 to 30% by mass.

5. The process as claimed in claim 1, wherein the at least one second isobutene-containing hydrocarbon mixture has a water content which is not more than 10% above the content which is soluble in the hydrocarbon mixture.

6. The process as claimed in claim 1, wherein one reactor is supplied alternately with the at least two different isobutene-containing hydrocarbon mixtures.

7. The process as claimed in claim 1, wherein at least two reactors are connected in parallel to form a reactor unit and are supplied with the two different isobutene-containing hydrocarbon mixtures.

8. The process as claimed in claim 7, wherein the at least two reactors comprise at least two different ouputs and the at least two outputs are together separated in one distillation unit into a hydrocarbon-containing stream and crude tert-butanol.

9. The process as claimed in claim 7, wherein the at least two reactors comprise at least two different ouputs and the at least two outputs are fractionated separately in two distillation units to give hydrocarbon-containing streams and crude tert-butanol and a overhead product having a higher isobutene content is supplied to an alternately operated reactor.

10. The process as claimed in claim 1, wherein at least two reactors or reactor units are operated alternately.

11. The process as claimed in claim 1, wherein the alternating supply to the at least one reactor is effected so that the mixtures are changed in a cycle of from 0.5 to 10 hours.

12. The process as claimed in claim 1, wherein the at least a first isobutene-containing hydrocarbon mixture and the at least a second isobutene-containing hydrocarbon mixture is supplied to the at least one reactor at a time ratio of greater than or equal to 1.

13. The process as claimed in claim 12, wherein the at least a first isobutene-containing hydrocarbon mixture and the at least a second isobutene-containing hydrocarbon mixture is supplied to the at least one reactor at a time ratio of from 1.5:1 to 2.5:1 is set.

14. The process as claimed in claim 1, which is carried out at a temperature of from 30 to 120° C.

15. The process as claimed in claim 1, wherein the process is carried out in at least two reactors forming a reactor cascade.

16. The process as claimed in claim 15, wherein a hydrocarbon mixture having an isobutene content of greater than 25% by mass is fed into a first reactor of the reactor cascade.

17. The process as claimed in claim 15, wherein, the at least two reactors of the reactor cascade are not operated alternately, and wherein water is fed in before the mixture enters the reactors.

18. The process as claimed in claim 15, wherein the at least two reactors of the reactor cascade are operated such that a temperature difference of the mixture from a reactor inlet to a reactor outlet is less than 10 K.

19. The process as claimed in claim 1, wherein the at least one reactor is operated at a linear velocity of from 1 to 60 m/h, and wherein the solid acid catalyst is an ion-exchange resin having a mean particle size of from 0.1 to 5 mm.

20. The process as claimed in claim 15, wherein the at least one reactor which is supplied alternately with at least two different isobutene-containing hydrocarbon mixtures is the last reactor or a last reactor unit comprising two or more reactors connected in parallel of the reactor cascade.

* * * * *